(12) United States Patent
Kraus (10) Patent No.: US 7,288,863 B2
(45) Date of Patent: Oct. 30, 2007

(54) ELECTRIC APPLIANCES HAVING ELECTRIC MOTORS FOR DRIVING OSCILLATORY ELEMENTS

(75) Inventor: Bernhard Kraus, Braunfels (DE)

(73) Assignee: Bruan GmbH, Kronberg (DE)

( * ) Notice: Subject to any disclaimer, the term of this patent is extended or adjusted under 35 U.S.C. 154(b) by 0 days.

(21) Appl. No.: 11/328,329

(22) Filed: Jan. 9, 2006

(65) Prior Publication Data

US 2006/0175909 A1    Aug. 10, 2006

Related U.S. Application Data

(63) Continuation of application No. PCT/EP2004/06199, filed on Jun. 9, 2004.

(30) Foreign Application Priority Data

Jul. 9, 2003    (DE) ................. 103 30 978

(51) Int. Cl.
*H02K 33/00* (2006.01)
(52) U.S. Cl. .......................... 310/37; 310/38
(58) Field of Classification Search ........... 310/36–38, 310/47, 50
See application file for complete search history.

(56) References Cited

U.S. PATENT DOCUMENTS

| | | | | |
|---|---|---|---|---|
| RE25,934 E | * | 12/1965 | Chausson | 417/418 |
| 3,296,468 A | * | 1/1967 | Chambrey | 310/29 |
| 3,525,887 A | * | 8/1970 | Ewart, Jr. | 310/27 |
| 3,538,359 A | | 11/1970 | Barowski et al. | |
| 3,729,691 A | * | 4/1973 | Beiswinger et al. | 331/116 M |
| 3,906,263 A | * | 9/1975 | Chen et al. | 310/29 |
| 4,169,234 A | * | 9/1979 | Yonkers | 310/29 |
| 4,595,849 A | | 6/1986 | Cuenoud | |
| 5,028,856 A | * | 7/1991 | Zannis | 318/687 |
| 5,189,751 A | * | 3/1993 | Giuliani et al. | 15/22.1 |
| 5,736,797 A | * | 4/1998 | Motohashi et al. | 310/36 |
| 5,833,440 A | * | 11/1998 | Berling | 417/418 |

FOREIGN PATENT DOCUMENTS

| | | |
|---|---|---|
| CH | 265598 | 3/1950 |
| DE | 1 151 307 | 7/1963 |
| DE | 197 81 664 | 8/2001 |
| DE | 196 80 506 | 10/2002 |
| EP | 0 674 979 | 3/1997 |
| EP | 1 193 844 | 4/2002 |
| FR | 2 179 653 | 11/1973 |
| GB | 847156 | 7/1960 |

* cited by examiner

*Primary Examiner*—Dang Le
(74) *Attorney, Agent, or Firm*—Fish & Richardson P.C.

(57) ABSTRACT an electric appliance includes an electric motor having a first oscillatory element, a second oscillatory element and an electric coil configured to generate a magnetic field to drive the first and second oscillatory elements. The electric appliance also includes a movable component and a first spring element connecting the movable component to the first oscillatory element. Notably, the first oscillatory element and the second oscillatory element are arranged to drive each other in oscillatory motions of opposite phase in response to the magnetic field of the electric coil.

25 Claims, 5 Drawing Sheets

ELECTRIC APPLIANCES HAVING ELECTRIC MOTORS FOR DRIVING OSCILLATORY ELEMENTS

REFERENCE TO RELATED APPLICATIONS

This application is a continuation of PCT application PCT/EP2004/006199, filed Jun. 9, 2004 and designating the United States, and claims priority under 35 USC §119(a) from German patent application 103 30 978.0, filed Jul. 9, 2003. The complete disclosures of both priority applications are incorporated herein by reference.

TECHNICAL FIELD

This disclosure relates to electric appliances, e.g., electric shavers and electric toothbrushes, having electric motors for driving oscillatory elements.

BACKGROUND

Electric appliances, e.g., electric shavers and electric toothbrushes, having electric motors for driving oscillatory motor components are known in the art. For example, a device of this type is described in DE 1 151 307 A, which discloses an oscillating armature drive for a dry shaving apparatus. The oscillating armature drive includes a reciprocating shaving cutter and a U-shaped electromagnet formed fast with a housing of the shaving apparatus. A working armature and compensating armatures, adjacent the working armature on opposite sides, are arranged near the poles of the electromagnet. In operation, the working armature, which drives the shaving cutter, oscillates parallel to the pole faces of the electromagnet, and the compensating armatures oscillate in phase opposition to the working armature to prevent the transmission of oscillations from the working armature to the housing of the shaving apparatus.

As another example, DE 196 80 506 T1 discloses an electric shaving apparatus having a linear oscillation motor with a stationary electromagnet and a plurality of movable components that are set in oscillatory motion in phase opposition to each other by the electromagnet. The movable components are interconnected by a linkage mechanism that transfers the oscillatory motion from one movable component to another with simultaneous reversal of direction.

DE 197 81 664 C2 discloses an electric shaver with a linear drive that has a hollow cylindrical stator with an electromagnetic coil. Arranged in the stator are two movable elements that are driven in phase opposition to each other, the one element driving a shaving cutter while the other element may have a counterweight to suppress vibrations.

EP 1 193 844 A1 discloses a linear oscillator. A housing, constructed as a stator, accommodates a rotor that executes a reciprocating motion. A movable spindle, contained with the housing, controls the amplitude of oscillation of the rotor. The rotor and the spindle are coupled to each other and to the housing by springs. The oscillatory motion generated by the linear oscillator can be transferred to either the rotor or the spindle, thereby reducing the transmission of oscillatory motions to the housing.

SUMMARY

Various aspects of this invention include an electric motor having a first oscillatory element, a second oscillatory element and an electric coil, wherein the first oscillatory element and the second oscillatory element drive each other in oscillatory motions of opposite phase upon exposure to a magnetic field generated by the electric coil.

According to one aspect, an electric appliance includes an electric motor having a first oscillatory element, a second oscillatory element and an electric coil configured to generate a magnetic field to drive the first and second oscillatory elements. The electric appliance also includes a movable component and a first spring element connecting the movable component to the first oscillatory element. Notably, the first oscillatory element and the second oscillatory element are arranged drive each other in oscillatory motions of opposite phase in response to the magnetic field of the electric coil.

According to this aspect, the electric motor generates oscillatory motions in both the first oscillatory element and the second oscillatory element without additional provisions. In addition, the connection of the movable component to the first oscillatory element through the first spring element allows for the transmission of oscillatory movement from the first oscillatory element to the movable component. Therefore, an electric motor of comparatively simple construction can be used to produce a number of different drive motions adapted to the particular application.

In some cases, a second spring element elastically connects the first oscillatory element to the second oscillatory element. Preferably, the second spring element has a spring rate that is greater than a spring rate of the first spring element.

In some examples, the movable component is configured for oscillatory movement. Preferably, the movable component and the first oscillatory element oscillate in phase opposition to each other.

In one embodiment, the movable component includes a first working unit, which is driven by the oscillatory motions of the first oscillatory element transferred through the first spring element. In accordance with this embodiment, the electric appliance may include a second working unit drivably connected to the electric motor. The second working unit may be rigidly connected to one of the first oscillatory element and the second oscillatory element. Preferably, the first and second working units oscillate in phase opposition to each other so as to avoid any unwelcome vibrations of an appreciable magnitude. In some cases, the first and second working units have differing resonant frequencies and/or differing amplitudes of oscillation. In some cases, the amplitudes of oscillation of the first and second working units are individually controllable through the electric coil. This allows for adaptation of the electric motor according to the particular operating situation.

In some instances, the movable component includes a balance weight. The balance weight serves to compensate for vibrations resulting from the oscillatory movements of the first oscillatory element.

In some cases, one of the first oscillatory element and the second oscillatory element includes a magnetizable core, and wherein the electric coil is wound about the magnetizable core to form an electromagnet.

In some embodiments, the first oscillatory element and the second oscillatory element are configured for linear oscillatory movement. In this case, the electric appliance can be an electric shaver.

In other embodiments, the first oscillatory element and the second oscillatory element are configured for rotary oscillatory movement. In some cases, the electric motor is configured for continuous rotary motion. In some examples, the electric appliance is an electric toothbrush.

According to another aspect, an electric shaver has an electric motor that includes a first oscillatory element having a magnetizable core and an electric coil, wound about the magnetizable core, configured to generate a magnetic field; and a second oscillatory element. The electric shaver also includes a shaving head and a first spring element elastically connecting the shaving head to one of the first oscillatory element and the second oscillatory element. Notably, the first oscillatory element and the second oscillatory element drive each other in linear oscillatory motions of opposite phase upon exposure to the magnetic field of the coil.

In some cases, the electric shaver also includes a second spring element elastically connecting the first oscillatory element to the second oscillatory element.

In some embodiments, the shaving head includes a shaving foil.

In some implementations, the electric shaver also includes a shaving cutter rigidly connected to one of the first oscillatory element and the second oscillatory element. In some cases, the shaving cutter and the shaving head are configured to oscillate in phase opposition to each other. In some examples, the shaving cutter and the shaving head are both connected to the same one of the first oscillatory element and the second oscillatory element.

In yet another aspect, a method of controlling an electric appliance includes providing an electric appliance having an electric motor that includes a first oscillatory element, a second oscillatory element, and an electric coil configured to generate a magnetic field to drive the first and second oscillatory elements. The method includes connecting a first working unit to one of the first oscillatory element and the second oscillatory element by way of a first spring element. The method also includes supplying a flow of current through the electric coil, thereby generating a magnetic field to drive the first and second oscillatory elements; and reversing the flow of current through the electric coil, thereby reversing a polarity of the magnetic field causing the first oscillatory element and the second oscillatory element to be set in oscillations of opposite phase.

Other features and advantages of the invention will be apparent from the following detailed description, and from the claims.

DETAILED DESCRIPTION

Figure 1:
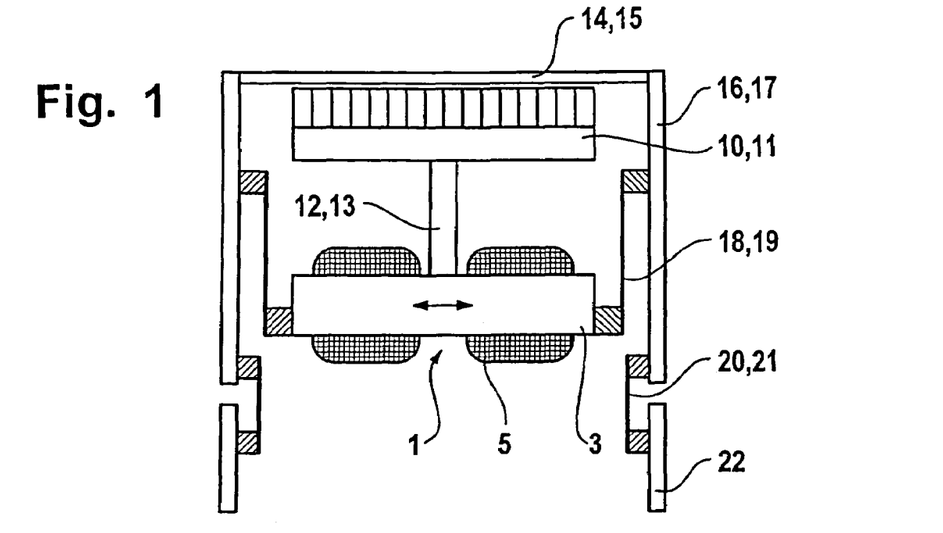
FIG. 1 is a schematic side view of an embodiment of an electric shaver comprising a statorless linear electric motor.
Figure 2:
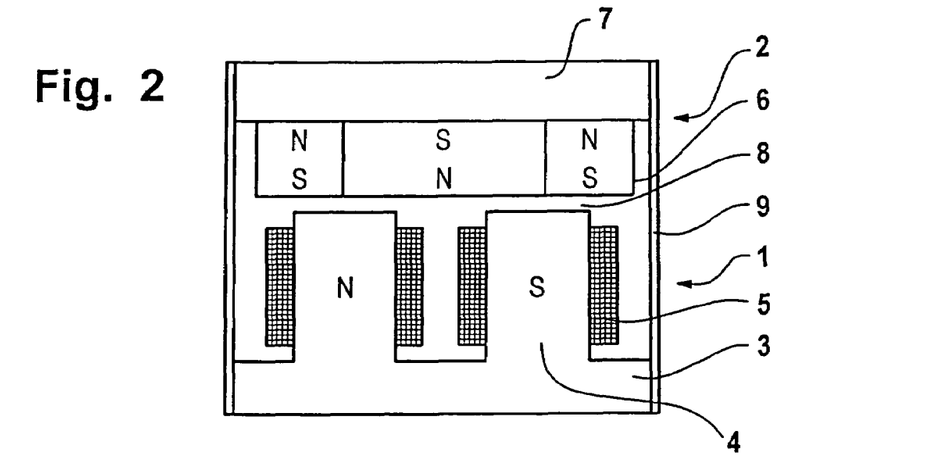
FIG. 2 is a schematic plan view of the statorless linear electric motor of the electric shaver of FIG. 1.

FIG. 1 shows, in a schematic side view, an embodiment of an electric shaver having a statorless linear electric motor. A related schematic plan view of the statorless linear electric motor is shown in FIG. 2. The statorless linear electric motor includes a first oscillatory element or rotor 1 and a second oscillatory element or rotor 2 spaced from each other. The first rotor 1 includes an iron core 3 having two legs 4 extending in the direction of the second rotor 2. Arranged on each leg 4 is a wire-wound coil 5, with the coils 5 being operable either as separate individual coils or as a shared coil. The second rotor 2 includes three permanent magnets 6 arranged side by side with antiparallel polarity on a common carrier plate 7, such that one of the magnetic poles points toward the iron core 3 of the first rotor 1. Like the iron core 3, the carrier plate 7 is made of an iron material. As illustrated in FIG. 2, the first rotor 1 and the second rotor 2 are arranged side-by-side in close proximity to each other, such that the permanent magnets 6 are separated from the respective end of the respective neighboring leg 4 of the iron core 3 by a small air gap 8. The width of the air gap 8 is determined by first leaf springs 9 mounted on the sides of the iron core 3 and the carrier plate 7. Referring to FIG. 2, the first leaf springs 9 can operate as rigid bodies in the plane defined by them while yielding elastically in a perpendicular plane. Therefore, the first rotor 1 and the second rotor 2, in response to a force produced by the first leaf springs 9, may perform relative oscillatory movements to the left and right (shown in FIG. 1 as a double arrow) while their relative distance, and hence the width of the air gap 8, is maintained substantially unchanged. An oscillatory system is thereby obtained in which the first rotor 1 and the second rotor 2 each operate in a linear oscillatory motion. The directions of movement of the first rotor 1 and the second rotor 2 are opposed to one another, that is, the oscillations are in phase opposition to each other.

The oscillations are set in motion and maintained by a current flowing through the coils 5. The coils 5 act as electromagnets, with the assistance of the iron core 3, generating a magnetic field that acts on the permanent magnets 6 producing a relative movement between the coils 5 and the permanent magnets 6. By controlling the flow of current through the coils 5 it is possible to reverse the polarity of the respective magnetic field produced with the coils 5, causing the first rotor 1 and the second rotor 2 to be set in oscillations of opposite phase. Therefore, the electric motor is capable of performing a driving function similar to that of a linear motor having a stationary stator; however, the first rotor 1 and the second rotor 2 of the statorless linear electric motor can oscillate at a relative speed that is twice as high as the relative speed of a stator and a rotor of a linear motor having a stationary stator. A relatively high degree of efficiency is thus accomplishable.

In the embodiment shown in FIG. 1, the first rotor 1 drives a first shaving cutter 10 (i.e., a first working unit) and the second rotor 2 drives a second shaving cutter 11 (i.e,. a second working unit) of the electric shaver. As illustrated in FIG. 1, the first shaving cutter 10 is rigidly connected to the first rotor 1 by a first connecting member 12, and the second shaving cutter 11 is connected to the second rotor 2 by a second connecting member 13. In FIG. 1, the shaving cutters 10, 11, as well as the connecting members 12, 13, are arranged one behind the other and hence not visible as individual parts. Referring still to FIG. 1, a first shaving foil 14 (i.e,. a third working unit) and a second shaving foil 15 (i.e,. a fourth working unit) are integrated in a first shaving head part 16 and a second shaving head part 17, respectively. The first shaving head part 16 is connected to the first rotor 1 by second leaf springs 18. The second shaving head part 17 is connected to the second rotor 2 by third leaf springs 19. The first shaving head part 16 and the second shaving head part 17 are movably suspended on a housing 22 of the electric shaver by fourth leaf springs 20 and fifth leaf springs 21, respectively. The leaf springs 9, 18, 19, 20 and 21 are graded in their stiffness such that the first leaf springs 9 are the stiffest. The second leaf springs 18 and third leaf springs 19 are of like stiffness grade and somewhat weaker than the first leaf springs 9. The fourth leaf springs 20 and the fifth leaf springs 21 are of like stiffness grade, but weaker than the second and third leaf springs 18, 19. The oscillatory system, as described above, is illustrated in FIG. 3.

Figure 3:
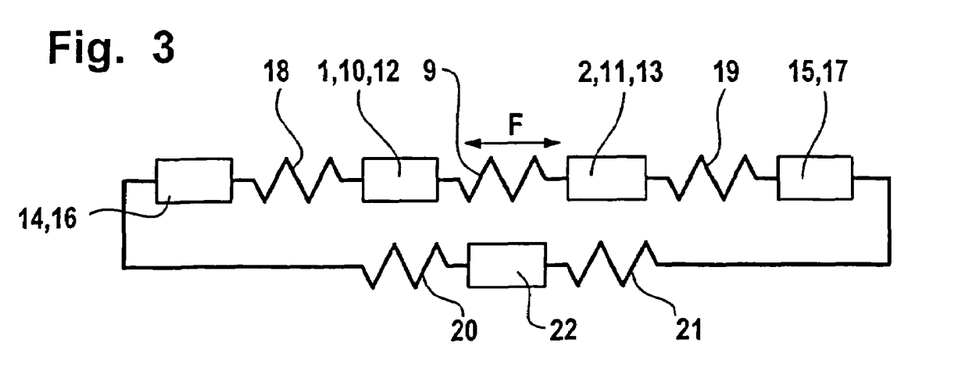
FIG. 3 is a block diagram of the oscillatory system formed by the components illustrated in FIG. 1.

FIG. 3 shows a block diagram of the oscillatory system formed by the components illustrated in FIG. 1. In this arrangement, the individual blocks are representative of the masses of the jointly moving components and are correspondingly identified by the reference numerals of the associated components. The leaf springs 9, 18, 19, 20 and 21 are represented by spring symbols drawn between adjacent blocks. Finally, the magnetic force F acting between the first rotor 1 and the second rotor 2 is shown in the form of a double arrow. In the presence of a magnetic force F, preferably acting periodically with a resonant frequency of the rotors 1, 2 and the shaving cutters 10, 11, the rotors 1 and 2 and, in corresponding manner, the shaving cutters 10 and 11, are set in oscillatory motions of opposite phase. The amplitude of oscillation of the rotors 1, 2, and the shaving cutters 10, 11 can be of the order of about 2 mm. The oscillations of the rotors 1, 2 are transmitted via the second and third leaf springs 18, 19 to the shaving head parts 16 and 17, respectively. Since the second and third leaf springs 18, 19 are weaker than the first leaf springs 9, the shaving head parts 16, 17 are excited to oscillate at significantly lower amplitudes than the first and second rotors 1, 2. The amplitudes of oscillation of the shaving head parts 16, 17 and hence also of the shaving foils 14, 15 can be of the order of about 0.2 mm. Moreover, the oscillations of the shaving foils 14, 15 are in phase opposition to the oscillations of the shaving cutters 10, 11. The fourth and fifth leaf springs 20, 21 transmit the oscillations of the shaving head parts 16,17 to the housing 22. Employing the fourth and fifth leaf springs 20, 21, having relatively weak spring stiffness, allows for reduction in the transmission of oscillatory motions to the housing 22. In addition, the phase opposition of the oscillations may also reduce the transmission of oscillatory motions to the housing.

Overall, with the statorless linear electric motor illustrated in FIG. 1, the first shaving cutter 10, the second shaving cutter 11, the first shaving foil 14 and the second shaving foil 15 can be set in oscillations of different magnitude each without the necessity of additional components. According to the embodiment of FIG. 1, the two shaving cutters 10, 11 oscillate in phase opposition to each other and in phase opposition to the associated shaving foils 14, 15.

Figure 4:
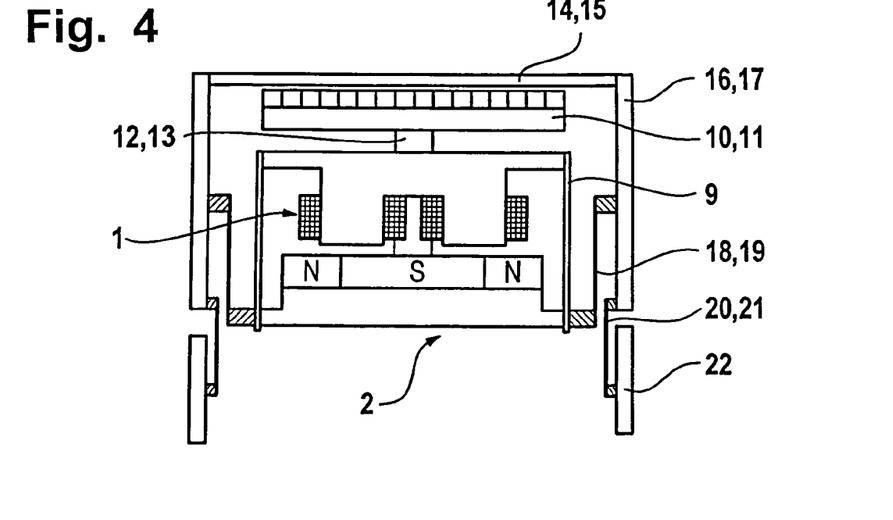
FIG. 4 a schematic side view of another embodiment of the electric shaver.

FIG. 4 shows a second embodiment of the electric shaver in a schematic side view. In contrast to FIG. 1, the statorless linear motor of the second embodiment is mounted in the electric shaver in a position rotated through 90 degrees, that is, as shown in FIG. 4, the first rotor 1 and the second rotor 2 are not arranged one behind the other but one above the other. Again, the two rotors 1 and 2 are connected to each other by first leaf springs 9. The first shaving cutter 10 (i.e., a first working unit) and the second shaving cutter 11 (i.e., a second working unit) are connected to the second rotor 2 by the first connecting member 12 and the second connecting member 13, respectively. The first shaving foil 14 (i.e., a third working unit) and the first shaving head part 16 as well as the second shaving foil 15 (i.e., a fourth working unit) and the second shaving head part 17 are likewise connected to the second rotor 2 through second and third leaf springs 18, 19 in addition to being suspended on the housing 22 by means of fourth and fifth leaf springs 20, 21. According to the embodiment illustrated in FIG. 4, the first rotor 1 does not adopt a drive function but oscillates freely. The oscillatory action of the entire system will be explained in greater detail with reference to FIG. 5.

Figure 5:
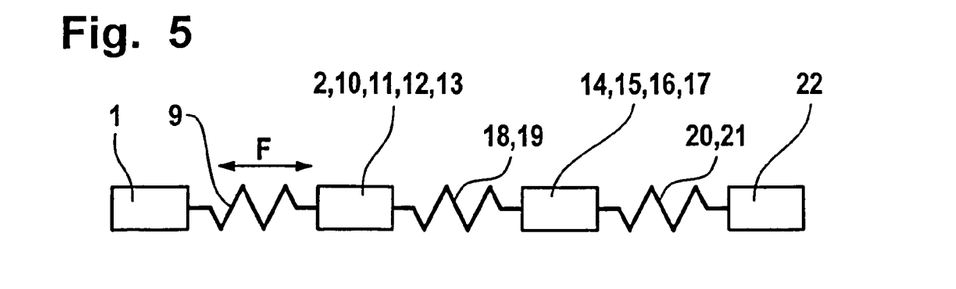
FIG. 5 is a block diagram of the oscillatory system formed by the components illustrated in FIG. 4.

FIG. 5 shows a block diagram of the oscillatory system formed by the components illustrated in FIG. 4. The oscillatory action depends on the ratio of the mass of the first rotor 1 to the mass of the second rotor 2 including the connecting members 12, 13 and the shaving cutters 10,11. If the masses are of different magnitude, correspondingly different amplitudes of oscillation of the first rotor 1 and the second rotor 2 will develop by reason of pulse maintenance. In order to prevent the amplitude of oscillation of the first shaving cutter 10 and the amplitude of oscillation of the second shaving cutter 11 from substantially dropping under load, the spring forces of the first leaf springs 9 should be significantly greater than the friction forces of the shaving cutters 10 and 11 on the shaving foils 14 and 15. Preferably, a mass center of gravity of the first rotor 1, a mass center of gravity of the second rotor 2 including the connecting members 12, 13 as well as the shaving cutters 10, 11, and a mass center of gravity of the shaving head parts 16, 17 including the shaving foils 14, 15 should lie one above the other in a rest position. The oscillatory motions of these three mass centers of gravity are shown in FIG. 6.

Figure 6:
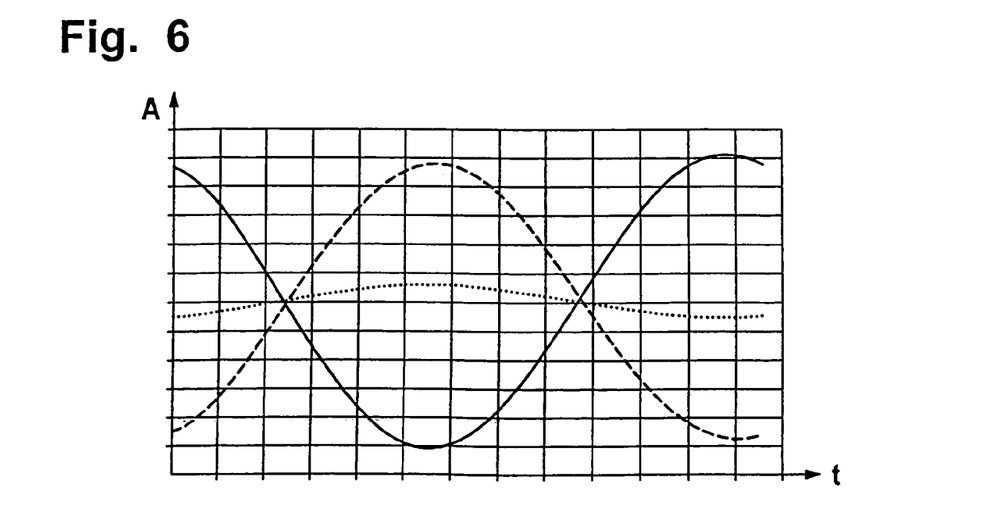
FIG. 6 is a graph showing the oscillatory motions of the mass centers of gravity of a first oscillatory element a second oscillatory element, including connecting members (i.e., springs), and movable components.

FIG. 6 shows a diagram of the oscillations of the mass centers of gravity of components or groups of components of the embodiment of the electric shaver illustrated in FIG. 4. Time t is plotted on the abscissa, and the excursion A of the mass centers of gravity from the rest position is plotted on the ordinate. The oscillation of the mass center of gravity of the first rotor 1 is illustrated as a broken line. The oscillation performed by the mass center of gravity of the second rotor 2 including the connecting members 12, 13 and the shaving cutters 10, 11 is shown as a solid line. The dotted line represents the oscillation of the mass center of gravity of the shaving head parts 16, 17 including the shaving foils 14, 15. For purposes of illustration, the masses of the first rotor 1 and the second rotor 2 including the components connected therewith were selected to be equal, so that the first rotor 1 and the second rotor 2 oscillate in phase opposition to each other with the same amplitude of oscillation. Similarly, the shaving head parts 16, 17 including the shaving foils 14, 15 oscillate in phase opposition to the second rotor 2, however with a substantially lower amplitude of oscillation.

Figure 7:
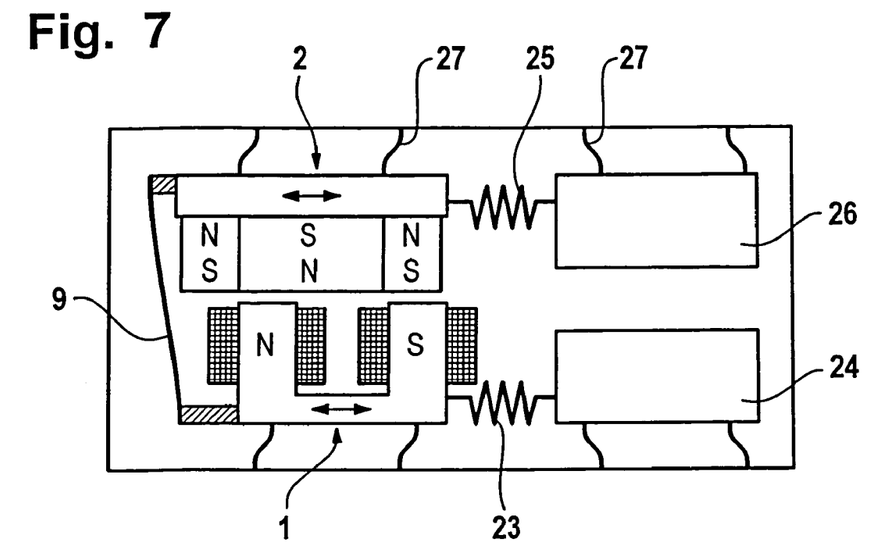
FIG. 7 is a schematic side view of an embodiment of a statorless linear electric motor for two different oscillation frequencies.

FIG. 7 shows an embodiment of a statorless linear motor for two different oscillation frequencies in a schematic side view. In this embodiment, the first rotor 1 is connected to a first balance weight 24 via a first helical spring 23, while a second helical spring 25 connects the second rotor 2 to a second balance weight 26. The helical springs 23, 25 can have a substantially greater spring constant than a first leaf spring 9, which connects the first rotor 1 to the second rotor 2. Both the rotors 1, 2 and the balance weights 24, 26 are linearly movably suspended on the housing 22 by second leaf springs 27 having a relatively weak spring stiffness, thereby reducing the transmission of oscillatory motions to the housing 22. The first rotor 1, the first helical spring 23 and the first balance weight 24 on the one side and the second rotor 2, the second helical spring 25 and the second balance weight 26 on the other side each form an oscillatory system which can be excited to oscillate by the application of a suitable voltage signal to the coils 5. If the two oscillatory systems are configured to have different resonant frequencies, these can be excited selectively through two suitable excitation frequencies in the voltage signal, thereby allowing the amplitudes of oscillation of the two oscillatory systems to be influenced individually. Correspondingly, the amplitudes of oscillation of the shaving cutters 10, 11 as well as the amplitudes of oscillation of the shaving foils 14, 15 can also be influenced. This possibility of individual control through adjustment of the voltage signal may also find application, for example, in the embodiment illustrated in FIG. 4 and in further embodiments of the invention.

Figure 8:
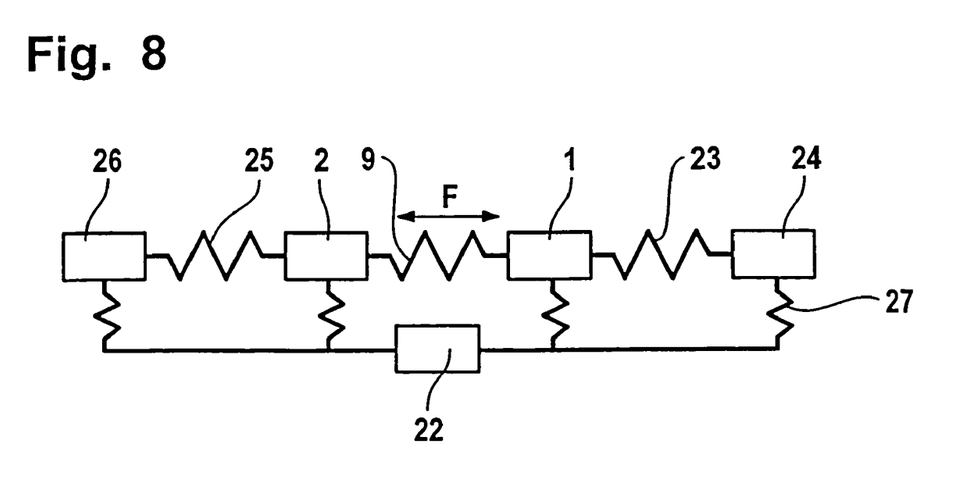
FIG. 8 is a block diagram of the statorless linear electric motor illustrated in FIG. 7.

FIG. 8 shows a block diagram of the statorless linear motor illustrated in FIG. 7. The first rotor 1 and the first balance weight 24 execute oscillatory motions in phase opposition to each other. Similarly, the second rotor 2 and the second balance weight 26 oscillate in phase opposition to one another. These opposite-phase relationships can reduce the transmission of oscillatory motions to the housing 22. Preferably, the frequencies of these oscillatory motions correspond to the resonant frequencies of the two oscillatory systems. The amplitudes of oscillation can be influenced individually through the driving of the coil 5.

Figure 9:
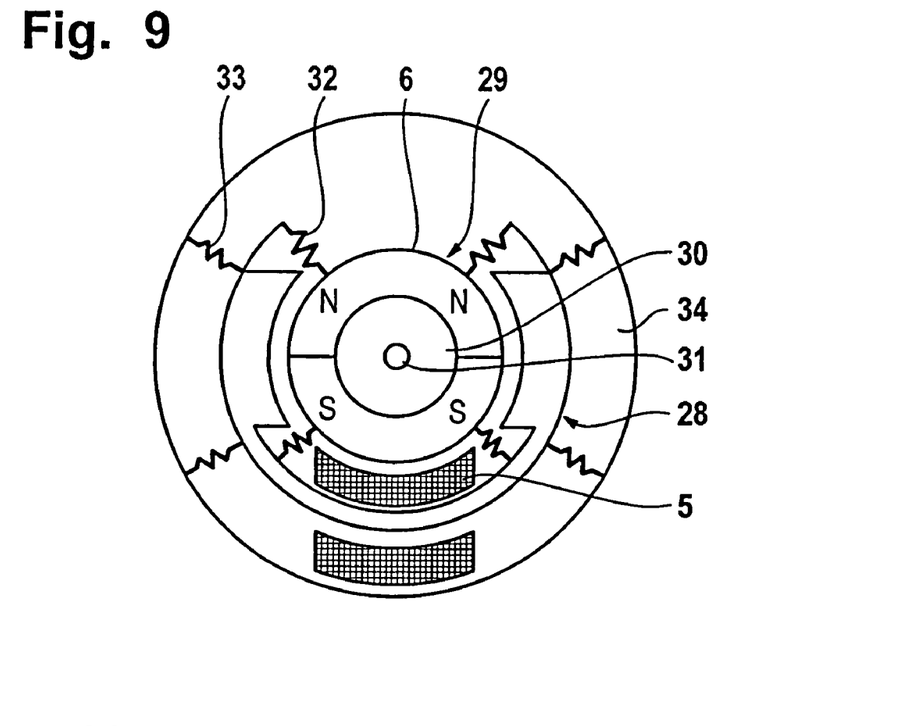
FIG. 9 is a schematic side view of an embodiment of a statorless rotary electric motor.

FIG. 9 shows an embodiment of a statorless rotary motor in a schematic side view. The statorless rotary motor has function components similar to those of the statorless linear motor. However, these function components are modified such that a rotary motion is produced instead of a linear motion. Thus the statorless rotary motor includes an outer rotor 28 which is rotatably suspended and made of an iron material. The outer rotor 28 extends in part within the coil 5 without however touching it, thereby enabling the outer rotor 28 to be rotated relative to the stationary coil 5. Arranged within the outer rotor 28 is an inner rotor 29 having a rotor core 30 made of an iron material and permanent magnets 6 affixed thereto. The inner rotor 29 is likewise rotatably suspended, with the outer rotor 28 and the inner rotor 29 having a shared axis of rotation 31. Furthermore, the rotary motor also includes a series of first helical springs 32 arranged between the outer rotor 28 and the inner rotor 29 as well as second helical springs 33 arranged between the outer rotor 28 and a hollow cylindrical member 34. The hollow cylindrical member 34 may be a component part of the housing 22 or be suspended on the housing 22 through springs, not shown, and be connected with a toothbrush attachment in cases where an electric toothbrush is involved. The rotary motor thus has two resonant frequencies. With regard to the control of the rotary motor, the foregoing explanations relating to the control of the linear motor apply analogously. When the statorless rotary motor finds practical application in a small electric appliance, preferably one or several torsion springs is/are used, substituting the two sets of helical springs 32, 33.

Figure 10:
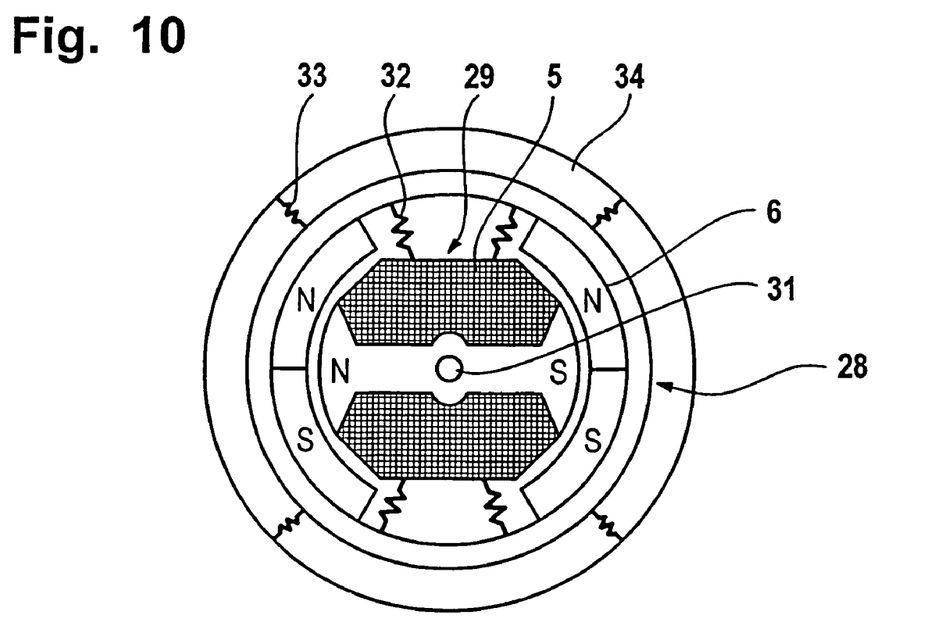
FIG. 10 is a schematic side view of another embodiment of the statorless rotary electric motor.

FIG. 10 shows another embodiment of the statorless rotary motor in a schematic side view. This embodiment differs from that of FIG. 9 in that the coil 5 is a component part of the inner rotor 29 and the permanent magnets 6 are component parts of the outer rotor 28.

Figure 11:
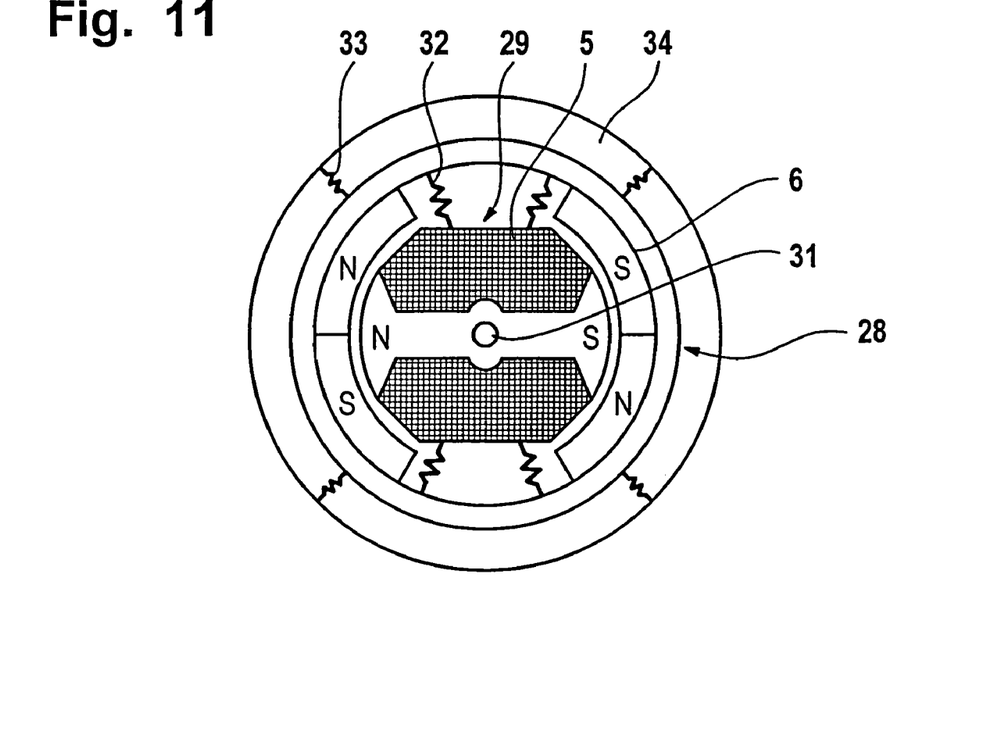
FIG. 11 is a schematic side view of an embodiment, once again modified in comparison with FIG. 10, of the statorless rotary electric motor.

FIG. 11 shows an embodiment, once again modified in comparison with FIG. 10, of the statorless rotary motor in a schematic side view. In this embodiment only the arrangement of the permanent magnets 6 differs from that of FIG. 10. By reason of the modified arrangement, the outer rotor 28 and the inner rotor 29 are excited to execute linear oscillations which in the representation of FIG. 11 extend in vertical direction.

Figure 12:
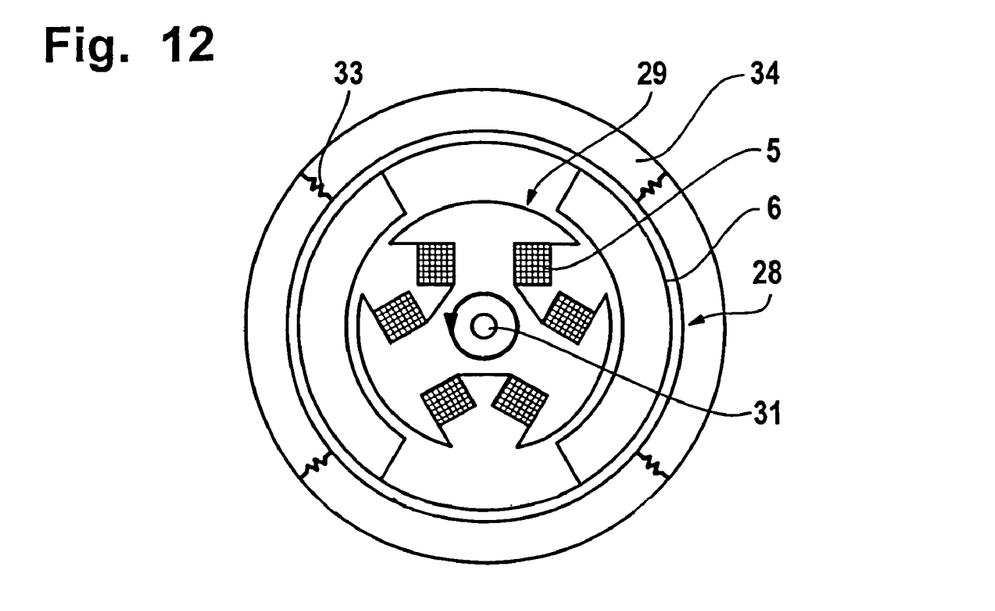
FIG. 12 is a schematic side view of an embodiment of a statorless rotary electric motor capable of executing a continuous rotary motion.

FIG. 12 shows an embodiment of a statorless rotary motor, capable of executing a continuous rotary motion, in a schematic side view. In this embodiment, the outer rotor 28 is equipped with the permanent magnets 6, and the inner rotor 29 includes several coils 5. The helical springs 33 are seated between the outer rotor 28 and the hollow cylindrical member 34. To enable the inner rotor 29 to rotate freely, no helical springs 32 are attached to it. The rotary motion of the inner rotor 29 is produced by alternately applying a DC voltage to the coils 5, which is accomplishable in known manner with the aid of electronic switch devices. Superimposed upon the DC voltage is an AC voltage, causing the outer rotor 28 to be excited to perform rotary oscillations which are transmitted through the helical springs 33 to the housing 22. Control is preferably such that the AC voltage amplitude does not exceed the DC voltage. The spring force of the helical springs 33 is selected to produce the desired oscillation of the hollow cylindrical member 34.

In a modified configuration an oscillatory motion is produced by providing the inner rotor 29 with an imbalance. The amplitude of oscillation can be influenced through selection of the rotary frequency of the inner rotor 29 relative to the resonant frequency of the oscillatory motion.

What is claimed is:

1. An electric appliance, comprising:
   a housing;
   an electric motor carried by the housing and including:
   a first oscillatory element,
   a second oscillatory element, and
   an electric coil configured to generate a magnetic field to drive the first and second oscillatory elements;
   a movable component; and
   a first spring element connecting the movable component to the first oscillatory element, wherein each of the first oscillatory element, the second oscillatory element, and the movable component are configured for oscillatory motion relative to each other, wherein the first oscillatory element and the second oscillatory element are configured to mutually drive each other in oscillatory motions of opposite phase with respect to the housing in response to the magnetic field of the electric coil, and wherein the oscillatory motions of the first oscillatory element drive the oscillatory motion of the movable component.

2. The electric appliance according to claim 1, further comprising a second spring element elastically connecting the first oscillatory element to the second oscillatory element.

3. The electric appliance according to claim 2, wherein a spring rate of the second spring element is greater than a spring rate of the first spring element.

4. The electric appliance according to claim 1, wherein the movable component is configured for oscillatory movement.

5. The electric appliance according to claim 4, wherein the movable component and the first oscillatory element oscillate in phase opposition to each other.

6. The electric appliance according to claim 5, wherein the movable component comprises a first working unit, and wherein the electric appliance further comprises a second working unit drivably connected to the electric motor.

7. The electric appliance according to claim 6, wherein the second working unit is rigidly connected to one of the first oscillatory element and the second oscillatory element.

8. The electric appliance according to claim 7, wherein the movable component and the second working unit oscillate in phase opposition to each other.

9. The electric appliance according to claim 7, wherein the first working unit and the second working unit have differing resonant frequencies.

10. The electric appliance according to claim 7, wherein the first working unit and the second working unit have differing amplitudes of oscillation.

11. The electric appliance according to claim 10, wherein the amplitudes or oscillation of the first working unit and the second working unit are individually controllable by the electric coil.

12. The electric appliance according to claim 1, wherein the movable component comprises a balance weight.

13. The electric appliance according to claim 1, wherein one of the first oscillatory element and the second oscillatory element comprises a magnetizable core, and wherein the electric coil is wound about the magnetizable core to form an electromagnet.

14. The electric appliance according to claim 1, wherein the first oscillatory element and second oscillatory element are configured for linear oscillatory movement.

15. The electric appliance according to claim 14, wherein the electric appliance is an electric shaver.

16. The electric appliance according to claim 1, wherein the first oscillatory element and the second oscillatory element are configured for rotary oscillatory movement.

17. The electric appliance according to claim 16, wherein the electric motor is configured to operate in a continuous rotary motion.

18. The electric appliance according to claim 16, wherein the electric appliance is an electric toothbrush.

19. An electric shaver, comprising:
a housing;
an electric motor carried by the housing and including:
a first oscillatory element,
a second oscillatory element, and
an electric coil configured to generate a magnetic field to drive the first and second oscillatory elements;
a shaving head; and
a first spring element connecting the shaving head to the first oscillatory element,
wherein each of the first oscillatory element, the second oscillatory element, and the shaving head are configured for oscillatory motion relative to each other, wherein the first oscillatory element and the second oscillatory element are configured to mutually drive each other in oscillatory motions of opposite phase with respect to the housing in response to the magnetic field of the electric coil and wherein the oscillatory motions of the first oscillatory element drive the oscillatory motion of the shaving head.

20. The electric shaver according to claim 19, further comprising a second spring element elastically connecting the first oscillatory element to the second oscillatory element.

21. The electric shaver according to claim 19, wherein the shaving head includes a shaving foil.

22. The electric shaver according to claim 19, further comprising a shaving cutter rigidly connected to one of the first oscillatory element and the second oscillatory element.

23. The electric shaver according to claim 22, wherein the shaving cutter and the shaving head are configured to oscillate in phase opposition to each other.

24. The electric shaver according to claim 22, wherein the shaving cutter and the shaving head are both connected to the same one of the first oscillatory element and the second oscillatory element.

25. A method of controlling an electric appliance, comprising:
providing an electric appliance including:
a housing;
an electric motor carried by the housing and comprising:
a first oscillatory element,
a second oscillatory element, and
an electric coil configured to generate a magnetic field to drive the first and second oscillatory elements;
connecting a movable component to one of the first oscillatory element and the second oscillatory element by way of a first spring element, wherein each of the first oscillatory element, the second oscillatory element, and the movable component are configured for oscillatory motion relative to each other, and wherein the oscillatory motion of the first oscillatory element drives the oscillatory motion of the movable component;
supplying a flow of current through the electric coil, thereby generating a magnetic field to drive the first and second oscillatory elements; and
reversing the flow of current though the electric coil, thereby reversing a polarity of the magnetic field causing the first oscillatory element and the second oscillatory element to mutually drive each other in oscillations of opposite phase with respect to the housing.

* * * * *